(12) United States Patent
Okawa et al.

(10) Patent No.: US 9,066,835 B2
(45) Date of Patent: Jun. 30, 2015

(54) ABSORBENT ARTICLE

(75) Inventors: Miyuki Okawa, Tokushima (JP); Akiko Tatsukawa, Tokushima (JP); Hirofumi Miyake, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 307 days.

(21) Appl. No.: 13/146,269

(22) PCT Filed: Mar. 16, 2010

(86) PCT No.: PCT/JP2010/001871
§ 371 (c)(1),
(2), (4) Date: Oct. 18, 2011

(87) PCT Pub. No.: WO2010/113398
PCT Pub. Date: Oct. 7, 2010

(65) Prior Publication Data
US 2012/0035565 A1  Feb. 9, 2012

(30) Foreign Application Priority Data

Mar. 30, 2009 (JP) ................... 2009-081942
Nov. 6, 2009 (JP) ................... 2009-255261
Dec. 19, 2009 (JP) ................... 2009-288527

(51) Int. Cl.
*A61F 13/53* (2006.01)
*A61F 13/505* (2006.01)
*A61F 13/535* (2006.01)

(52) U.S. Cl.
CPC ............. *A61F 13/505* (2013.01); *A61F 13/535* (2013.01)

(58) Field of Classification Search
CPC . A61F 13/505; A61F 13/535; A61F 13/5323; A61F 13/53436; A61F 13/53409; A61F 2013/53481; A61F 13/536

USPC .......................................................... 604/372
See application file for complete search history.

(56) References Cited

U.S. PATENT DOCUMENTS 3,667,466 A * 6/1972 Ralph .......................... 604/364
5,149,335 A * 9/1992 Kellenberger et al. ........ 604/372
(Continued)

FOREIGN PATENT DOCUMENTS

EP    0549988 A1   7/1993
EP    0615736 A1   9/1994
(Continued)

OTHER PUBLICATIONS

Premraj R et al., Biodegradation of Polymers, Indian Journal of Biotechnology (2005) 4:186-193.*
(Continued)

*Primary Examiner* — Susan Su
(74) *Attorney, Agent, or Firm* — Cermak Nakajima & McGowan LLP; Tomoko Nakajima

(57) ABSTRACT

The present invention provides an absorbent article that allows full use of the absorption performance of an absorbent polymer without inhibiting the swelling of the absorbent polymer due to the absorption of excreted body fluids, and that can be biodegraded with efficiency when it is disposed after use by burial in the soil or the like. The absorbent article includes at least one inner bag-like member, an absorbent polymer, and an outer bag-like member. The inner bag-like member is formed into a thin and substantially sheet-like form of a sheet having biodegradability and fluid permeability, and includes multiple accommodation spaces that are detached from the outside and separated from one another. The absorbent polymer has biodegradability and a substantially granular or powder form and is contained in each of the accommodation spaces in the inner bag-like member so as to be freely movable within the accommodation spaces.

4 Claims, 5 Drawing Sheets

(56) References Cited

U.S. PATENT DOCUMENTS

| | | | |
|---|---|---|---|
| 5,628,738 A * | 5/1997 | Suekane | 604/385.26 |
| 5,643,238 A * | 7/1997 | Baker | 604/368 |
| 5,863,288 A * | 1/1999 | Baker | 604/378 |
| 5,938,650 A | 8/1999 | Baer et al. | |
| 6,559,081 B1 * | 5/2003 | Erspamer et al. | 442/392 |
| 6,623,466 B1 * | 9/2003 | Richardson | 604/385.19 |
| 7,037,571 B2 * | 5/2006 | Fish et al. | 428/166 |
| 7,344,522 B2 | 3/2008 | Suzuki et al. | |
| 8,263,820 B2 * | 9/2012 | Carlucci et al. | 604/370 |
| 2003/0125694 A1 * | 7/2003 | Motta et al. | 604/385.04 |
| 2004/0220539 A1 * | 11/2004 | Glaug et al. | 604/367 |
| 2006/0069375 A1 * | 3/2006 | Waksmundzki et al. | 604/385.201 |
| 2007/0142802 A1 * | 6/2007 | Suzuki | 604/368 |
| 2011/0313384 A1 * | 12/2011 | Akiyama | 604/378 |
| 2012/0232508 A1 * | 9/2012 | Urushihara | 604/365 |
| 2013/0025795 A1 * | 1/2013 | Ukegawa et al. | 156/555 |

FOREIGN PATENT DOCUMENTS

| | | |
|---|---|---|
| JP | 2000-354609 A | 12/2000 |
| JP | 2003-070843 A | 3/2003 |
| JP | 2003-265522 A | 9/2003 |
| JP | 2006-102227 A | 4/2006 |
| JP | 2008-073187 A | 4/2008 |
| JP | 2009-131510 A | 6/2009 |
| WO | WO91/00077 A1 | 1/1991 |

OTHER PUBLICATIONS

Tokiwa et al., Biodegradability of Plastics, International Journal of Molecular Sciences (2009), 10:3722-3742.*

Leja et al., Polymer Biodegradation and Biodegradable Polymers—A Review, Polish J. of Environ. Stud. (2010) 19:255-266.*

International Search Report and Written Opinion for PCT Patent App. No. PCT/ JP2010/001871 (Aug. 18, 2010).

Patent Examination Report No. 1 from Australian Patent App. No. 2010231473 (Nov. 7, 2014).

Office Action from Taiwanese Patent App. No. 099106251 (Jan. 20, 2015) with English language translation thereof.

* cited by examiner

ABSORBENT ARTICLE

This application is a national phase entry under 35 U.S.C. §371 of PCT Patent Application No. PCT/JP2010/001871, filed on Mar. 16, 2010, which claims priority under 35 U.S.C. §119 to Japanese Patent Application No. 2009-081942, filed Mar. 30, 2009, Japanese Patent Application No. 2009-255261, filed Nov. 6, 2009, and Japanese Patent Application No. 2009-288527, filed Dec. 19, 2009, all of which are incorporated by reference.

TECHNICAL FIELD

The present invention relates to an absorbent article that absorbs excreted body fluids of a wearer.

BACKGROUND ART

The inventors of the present invention are working on the development of absorbent articles having compact and pad-like forms, for use in applications such as a replaceable absorptive member for incontinence pants or an absorptive member for reinforcing the absorbing capacity of a disposable diaper. This sort of absorbent article always has the problem of how it should be disposed after use, so a simple disposal method is desired.

As conventional techniques regarding diapers, there is a technique that enables a diaper to be disposed of by burial in the soil or the like by making the diaper from biodegradable materials (Patent Citation 1).

As conventional auxiliary absorptive members that reinforce the absorbing capacity of diapers or the like, Patent Citations 2 and 3 describe examples. For example, the absorbent article (laminated body (10)) described in Patent Citation 2 is configured by interposing an absorber (13) made of an absorbent polymer or the like between a top sheet (11) and a back side sheet (12) that have been joined to each other by thermal welding or the like (see paragraph [0013] and FIG. 2, of Patent Citation 2 for example). In the absorbent article described in Patent Citation 2, however, an accommodation space formed between the top sheet (11) and the back side sheet (12) provides the absorbent polymer with a low degree of flexibility and small space allowance at the time of swelling. This may inhibit the swelling of the absorbent polymer when excreted body fluids are absorbed, and may impair the absorption performance (absorbing capacity) of the absorbent polymer. The absorbent article further has poor handleability because, when it is inserted, a cumbersome task is necessary, such as folding the absorbent article so as to be inserted into a bag-like accommodating body (20).

CITATION LIST

Patent Literature

PTL 1: Japanese Patent Laid-open No. 2003-265522
PTL 2: Japanese Patent Laid-open No. 2000-354609
PTL 3: Japanese Patent Laid-open No. 2003-70843

SUMMARY OF INVENTION

Technical Problem

A first issue to be solved by the present invention is to provide an absorbent article that has good handleability when it is inserted or removed, can make full use of the absorption performance of an absorbent polymer without inhibiting the swelling of the absorbent polymer due to the absorption of excreted body fluids, and can be biodegraded with efficiency when it is buried in the soil or the like after use.

A second issue to be solved by the present invention is to provide an absorbent article that can make full use of the absorption performance of an absorbent polymer without inhibiting the swelling of the absorbent polymer due to the absorption of excreted body fluids, can be biodegraded with efficiency when it is buried in the soil or the like after use, can be easily separated into small pieces by hand, and can be easily disposed of by flushing it down a toilet or the like.

Solution to Problem

According to a first aspect of the absorbent article, at least one inner bag-like member that contains an absorbent polymer of a substantially granular or powder form in its internal accommodation space is contained in an outer bag-like member in either a layered or folded state. This achieves an absorbent article that provides sufficient absorbing capacity with a thin and compact structure and has good handleability when it is inserted or removed from incontinence pants, a diaper, or the like.

In addition, an absorbent polymer having a substantially granular or powder form is contained in each accommodation space in the inner bag-like member so as to be freely movable within the accommodation space. This ensures a sufficient space allowance for the swelling of the absorbent polymer caused by the absorption of excreted body fluids and consequently allows full use of the absorption performance of the absorbent polymer without inhibiting the swelling of the absorbent polymer.

In addition, since the absorbent polymer is freely movable within each accommodation space in the inner bag-like member, the absorbent article has a high degree of flexibility in its shape when it is fitted. As a result, the shape of the absorbent article can be changed freely depending on where the absorbent article is placed or the like, and accordingly the absorbent article can be used for various purposes. For example, the absorbent article according to the present invention may be provided in any arbitrary number on the inside of a tape- or pants-type diaper in order to reinforce the absorbing capacity of the diaper, for example. In this case, the absorbent article according to the present invention may be inserted so as to be sandwiched and held between the inner side of the diaper and the skin of a wearer (e.g., in the vicinity of a crotch portion or a discharging point), or a holder structure for holding the absorbent article according to the present invention may be provided on the skin-facing side of a diaper. Note that the above-described tape-type diaper refers to a diaper provided with a fastening member, such as a hook and loop fastener, for securing the diaper to the body of a wearer. The pants-type diaper refers to a sort of diaper which resembles a pair of pants that is put on by inserting legs through the leg holes.

In addition, since the absorbent article according to the present invention has a thin and compact structure, it is possible to reduce unpleasantness such as an oppressive sensation or a foreign body sensation that a wearer may feel due to the arrangement of an absorbent article when the absorbent article is arranged on the inside of a diaper, incontinence pants, or the like. For a wearer who has contracture of the body, a gap may be incurred due to body atrophy or the like between a diaper and the body, and urine or the like may leak outside through the gap. In such a case, it is preferable that a urinary pad or the like be placed on the inside of the diaper in order to prevent such incurrence of a gap, but in some cases, placing a urinary pad or the like may be difficult due to contracture of the body. Even in such a case where the placement of a urinary pad or the like is difficult due to contracture of the body, the absorbent article according to the present invention can be inserted between a diaper and the body, with a wearer wearing the diaper, so as to fill in the gap between the diaper and the body. Note that contracture refers to the state in which muscles have atrophied and thereby the articular range of motion has been limited because bedridden people, for example, do not move their legs.

In addition, at least one inner bag-like member containing an absorbent polymer is contained in the outer bag-like member. This eliminates the trouble of, for example, folding the absorbent article when the absorbent article is fitted in incontinence pants, a diaper, or the like, and also eliminates the need to accommodate the absorbent article in another bag-like body in order to keep the absorbent article in a folded state, thereby achieving good handleability at the time of fitting or removing the absorbent article.

In addition, since all materials for the inner bag-like member, the outer bag-like member, and the absorbent polymer included in the absorbent article according to the present invention are biodegradable materials, the used absorbent article can be disposed of by burial in the soil or the like. Moreover, since the absorbent polymer is separately contained in multiple accommodation spaces in the inner bag-like member, the absorbent polymer can be distributed and biodegraded with efficiency without being grouped in clusters when the absorbent article is disposed of by burial in the soil or the like. As a result, the whole absorbent article can be biodegraded with efficiency.

According to a second aspect of the absorbent article, a first sheet that forms the inner bag-like member has a higher basis weight than a second sheet that forms the outer bag-like member. This reduces the basis weight of the second sheet while preventing the absorbent polymer from leaking outside through the first sheet by narrowing gaps in the nonwoven fabric fiber of the first sheet. As a result, the material cost for the absorbent article can be reduced.

In addition, since the basis weight of the first sheet is higher than the basis weight of the second sheet, the absorbent polymer can be reliably sealed with the inner bag-like member without using non-biodegradable tissue paper for the first sheet. Note that, although being non-biodegradable, tissue paper has the property that its fiber is finer than a nonwoven fabric in normal cases.

According to a third aspect of the absorbent article, welding is used for every joint in the first sheet for forming the inner bag-like member and in the second sheet for forming the outer bag-like member, and accordingly no adhesive is used. This avoids impairment of the biodegradability of the absorbent article due to the use of an adhesive.

According to a fourth aspect of the absorbent article, since a break portion is formed by weakening a part of the bag-like member in order to make it breakable, the bag-like member can be separated into multiple pieces by breaking at the break portion. Hence, since the bag-like member can be easily separated into small pieces by hand, the used absorbent article can be easily disposed of by separating it into small pieces and flushing it down a toilet or the like. The absorbent article that has been separated into small pieces and flushed down a toilet or the like can be biodegraded in a water-purifier tank or the like.

According to a fifth aspect of the absorbent article, the break portion is provided along a partition portion that provides a partition between adjacent accommodation spaces in the bag-like member. This allows the formation of a break portion in the bag-like member without causing a decrease in strength or forming a hole or the like at a portion that forms an accommodation space in the bag-like member.

In addition, since the break portion is provided along the partition portion of the bag-like member, when the used bag-like member is separated at the break portion, the bag-like member can be separated into small pieces without breaking a portion that forms an accommodation space in the bag-like member. This avoids breakage of a portion that forms an accommodation space in the bag-like member when the bag-like member is separated, and thereby avoids the occurrence of inconvenience such as scattering of the absorbent polymer contained in an accommodation space.

According to a sixth aspect of the absorbent article, the absorbent article has a substantially long length extending in one direction. The absorbent article according to the present invention can thus be arranged in a region along a crotch portion or the like of a wearer on the inside of incontinence pants, a diaper, or the like, without giving any unpleasantness to the wearer. In particular, for a wearer who has contracture of the body, the absorbent article according to the present invention can be easily inserted into a crotch portion or the like of a wearer through the gap between a diaper and the skin side of the wearer, while the wearer is wearing the diaper.

DESCRIPTION OF EMBODIMENTS

An absorbent article according to a first embodiment of the present invention will be described with reference to FIGS. 1 to 3.

Figure 1:
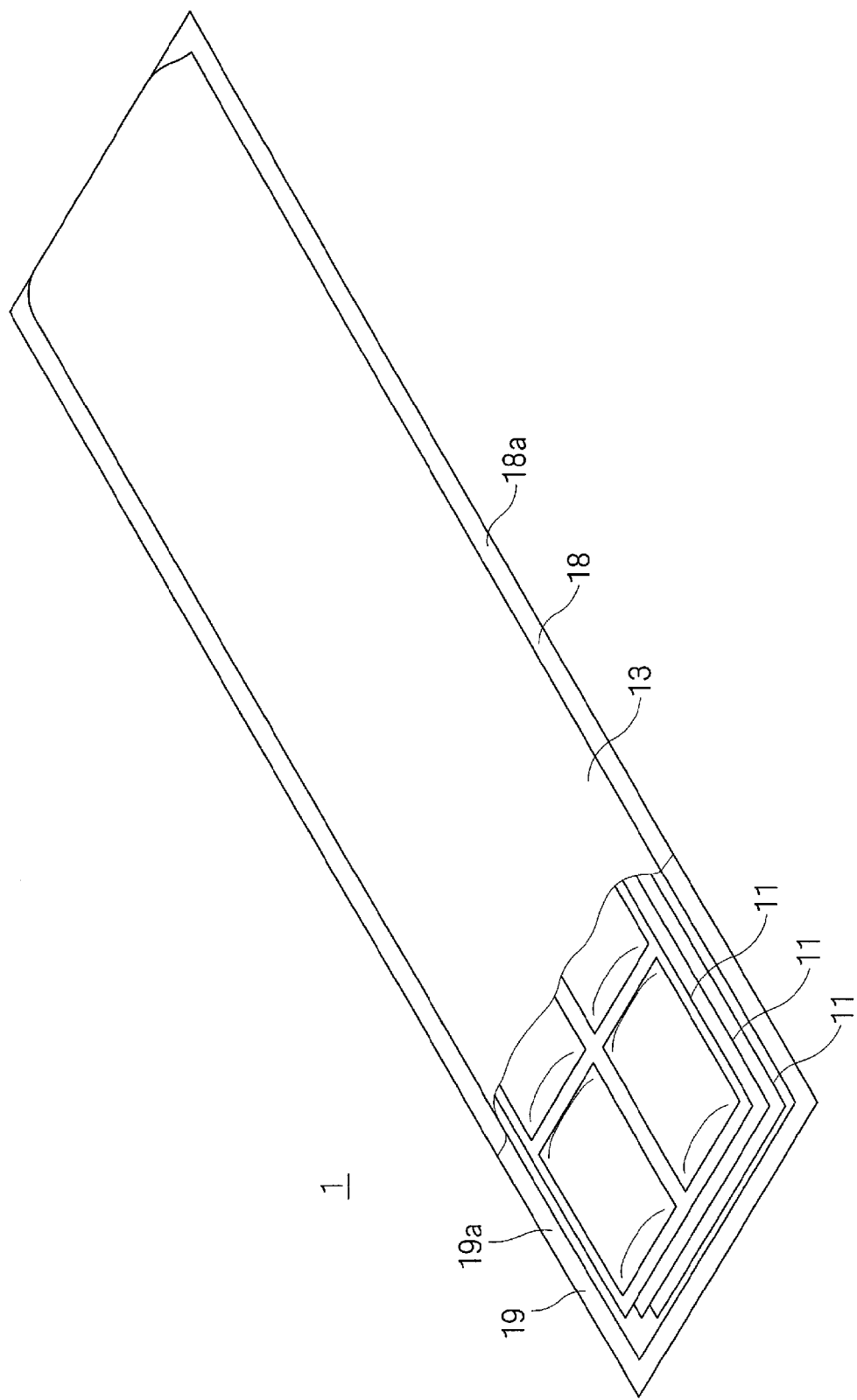
FIG. 1 is a cutaway perspective view of an absorbent article according to a first embodiment of the present invention.
Figure 2:
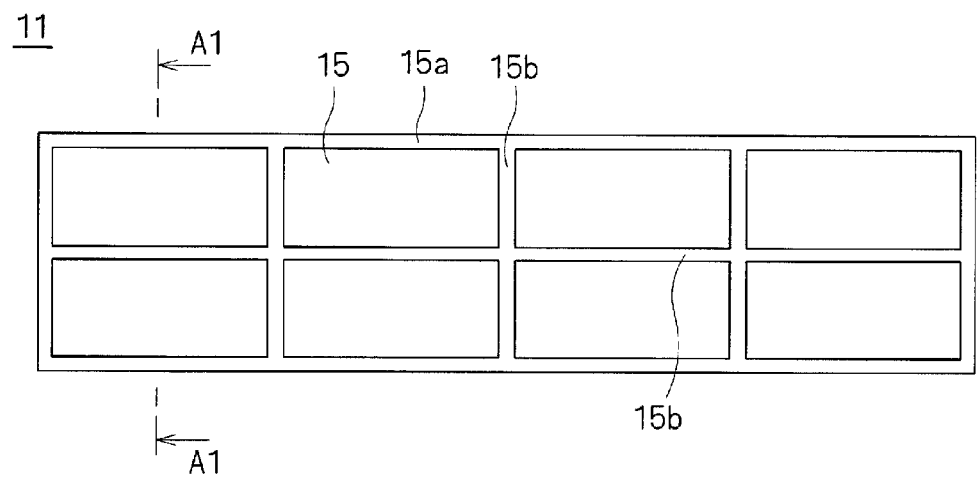
FIG. 2 is a plan view of an inner bag-like member of the absorbent article in FIG. 1.
Figure 3:
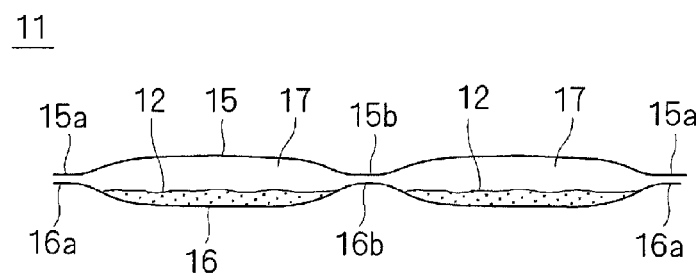
FIG. 3 is a view illustrating the structure in cross-section of the inner bag-like member taken along the line A1-A1 in FIG. 2.

An absorbent article 1 according to the present embodiment, as illustrated in FIGS. 1 to 3, includes multiple inner bag-like members 11, an absorbent polymer 12 contained in each of the inner bag-like members 11, and an outer bag-like member 13 that accommodates the multiple inner bag-like members 11. The absorbent article 1 is used to absorb excreted body fluids, such as moisture that is contained in urine or loose stools of a wearer, menstrual blood or the like. In the present embodiment, the absorbent article 1 is primarily used to absorb urine. All materials for the absorbent article 1 are biodegradable materials as will be described later, so that the used absorbent article 1 can be buried in the soil or the like. Note that, in the present embodiment, while the outer bag-like member 13 contains three inner bag-like members 11, the number of inner bag-like members 11 is not limited to three, and may be one, two, or more than three.

The inner bag-like members 11, as illustrated in FIGS. 2 and 3, have a thin and substantially sheet-like form and are formed of two first sheets 15 and 16 made of nonwoven fabric having biodegradability and fluid permeability. Inside the inner bag-like members 11, multiple accommodation spaces 17 are formed that are detached from the outside and separated from one another. The nonwoven fabric material for the first sheets 15 and 16 may be polylactate, for example.

The first sheets 15 and 16 have a substantially long-length, rectangular plan shape extending in one direction. Outer edge portions 15a and 16a of the two first sheets 15 and 16 are joined to each other by welding (heat welding or ultrasonic welding), and partition portions 15b and 16b that provide partitions between the multiple accommodation spaces 17 are joined to each other by welding (heat welding or ultrasonic welding). This produces the multiple accommodation spaces 17 that are detached from the outside and separated from one another in the inner bag-like members 11. Note that, in the present embodiment, heat welding is used for the welding of the sheets 15 and 16. Also note that, in the present embodiment, while eight accommodation spaces 17 are formed in two separate lines, the number of accommodation spaces 17 is not limited to eight. Alternatively, the accommodation spaces 17 may be formed in three or more separate lines, or may be formed in only a single line. Moreover, in the present embodiment, while the inner bag-like members 11 are formed of the two first sheets 15 and 16, they may be formed by folding a single first sheet 15 in two and joining the edges thereof together.

The absorbent polymer 12 has biodegradability and a substantially granular or powder form and is contained in each of the accommodation spaces 17 in each of the inner bag-like members 11 so as to be freely movable within the accommodation spaces 17. For this, the loading weight of the absorbent polymer 12 in each of the accommodation spaces 17 is set to a value at which enough surplus space is attained within each of the accommodation spaces 17. The material for the absorbent polymer 12 may be polyaspartic acid, for example.

The outer bag-like member 13, as illustrated in FIG. 1, is formed of two second sheets 18 and 19 made of nonwoven fabric having biodegradability and fluid permeability. In an accommodation space in the outer bag-like member 13, multiple inner bag-like members 11 are accommodated in a layered state. The nonwoven fabric material for the second sheets 18 and 19 may be polylactate, for example.

The second sheets 18 and 19 have a substantially long-length, rectangular plan shape extending in one direction. Outer edge portions 18a and 19a of the two second sheets 18 and 19 are joined to each other by welding (heat welding or ultrasonic welding). This produces a bag-like structure of the outer bag-like member 13. Note that, in the present embodiment, heat welding is used for the welding of the sheets 18 and 19. Also note that, in the present embodiment, while the outer bag-like member 13 is formed of the two second sheets 18 and 19, the outer bag-like member 13 may be formed by folding a single second sheet 18 in two and joining the edges thereof together.

Such configured absorbent article 1 has a thin and substantially long-length shape extending in one direction as illustrated in FIG. 1.

Moreover, in the present embodiment, the first sheets 15 and 16 that form the inner bag-like member 11 are set to have a higher basis weight than the second sheets 18 and 19 that form the outer bag-like member 13. This is in order to prevent the absorbent polymer 12 from leaking outside through gaps of the nonwoven fabric fiber of the sheets 15 and 16. For example, the basis weight of the first sheets 15 and 16 is set at approximately 30 grams per square meter, and the basis weight of the second sheets 18 and 19 is set at approximately 20 grams per square meter.

Figure 4:
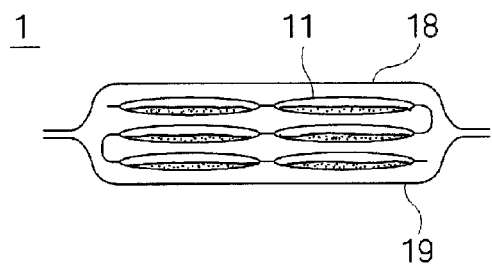
FIG. 4 is a cross-sectional view illustrating a variation of the absorbent article in FIG. 1.
Figure 5:
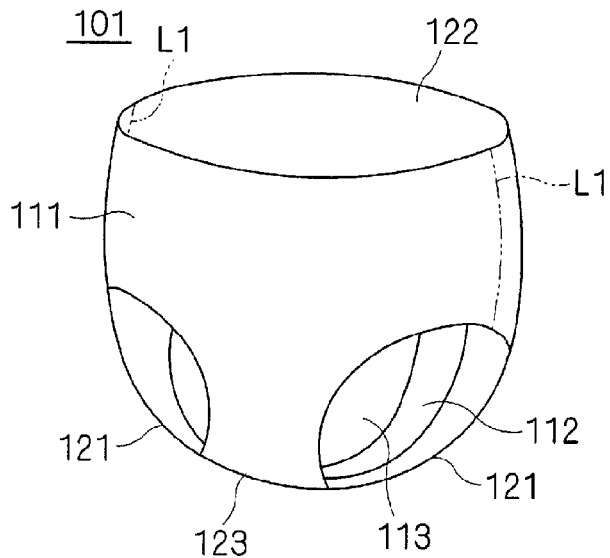
FIG. 5 is a perspective view of incontinence pants that use the absorbent article in FIG. 1.
Figure 6:
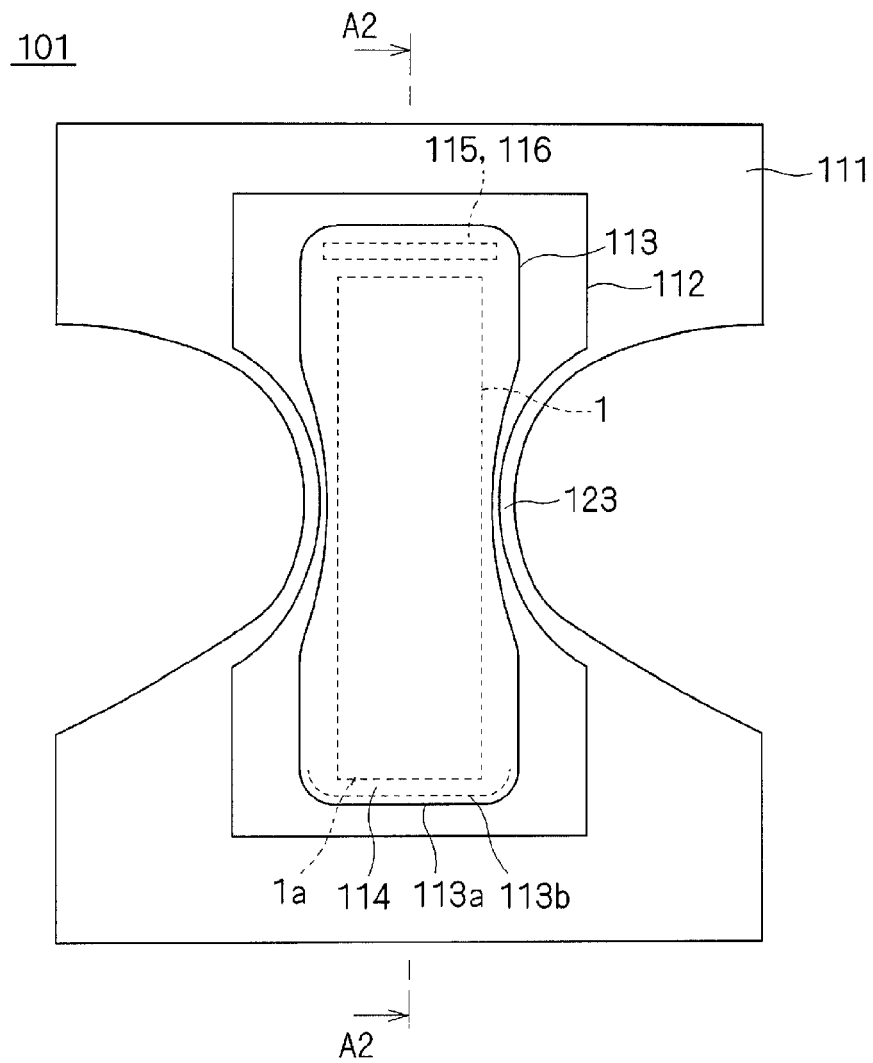
FIG. 6 is an expansion plane obtained by cutting right and left side portions (portions indicated by virtual lines L1 in FIG. 5) of the incontinence pants in FIG. 5.
Figure 7:
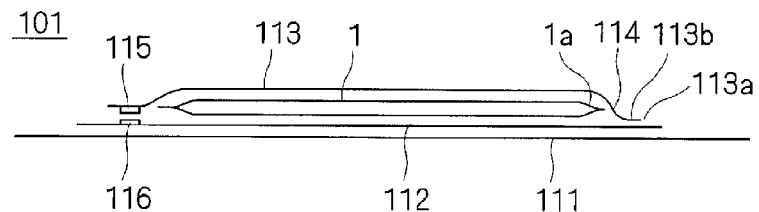
FIG. 7 is a cross-sectional view illustrating the structure in cross-section of the incontinence pants taken along the line A2-A2 in FIG. 5.

Note that, while the three inner bag-like members 11 that are separated from one another are accommodated in a layered state in the outer bag-like member 13 in the structure illustrated in FIG. 1, the structure illustrated in FIG. 4 is a variation with respect to this point. In the structure illustrated in FIG. 4, a single inner bag-like member 11 is folded along its longitudinal or lateral direction and accommodated in the outer bag-like member 13. As still another variation, multiple inner bag-like members 11 that have been folded in their longitudinal or lateral direction may be accommodated in the outer bag-like member 13.

Next, examples of the use of the absorbent article 1 according to the present embodiment will be described with reference to FIGS. 5 to 11. The absorbent article 1 according to the present embodiment is thin and compact and has a high degree of flexibility in its shape when it is fitted, because the absorbent polymer 12 is freely movable within the accommodation spaces 17 in the inner bag-like members 11. As a result, the shape of the absorbent article 1 can be changed freely depending on where the absorbent article 1 is placed or the like, and accordingly the absorbent article 1 can be used for various purposes.

For example, the absorbent article 1 according to the present embodiment may be applied to incontinence pants 101 as illustrated in FIGS. 5 to 8. Note that the upper side of the drawing in FIG. 6 corresponds to the front side of the incontinence pants 101.

The incontinence pants 101, as illustrated in FIGS. 5 to 8, includes a pants body 111, a waterproof sheet 112, a top sheet 113, a holding portion 114, and first and second securing portions 115 and 116, and the absorbent article 1 according to the present embodiment is removably put thereon. The incontinence pants 101 are washable and reusable.

The pants body 111 is formed by joining a single or multiple washable fabric materials by stitching or the like so as to form the outer shape of pants, and includes right and left leg holes 121 and a waist opening 122. The fabric material(s) for the pants body 111 may be woven fabric made of cotton, chemical fibers, or a fiber blend thereof, for example.

The waterproof sheet 112 is made of a fluid-impermeable material and secured by stitching, bonding, or the like so as to cover a region that includes a crotch portion 123 of the pants body 111 on the skin-facing side of the pants body 111. This waterproof sheet 112 prevents the urine absorbed by the absorbent article 1 from seeping through the incontinence pants 101.

The top sheet 113 is made of a sheet material having fluid permeability and has the absorbent article 1 sandwiched and held between itself and the waterproof sheet 112. A substantially U-shaped or substantially arc-shaped rear-side secured portion 113b of the top sheet 113 that extends along a rear-side outer edge 113a of the top sheet 113 is secured by stitching or the like to a portion located on the rear skin-facing side of the waterproof sheet 112. A portion of the top sheet 113 that is forward of the rear-side secured portion 113b, as illustrated in FIG. 8, is not secured to the waterproof sheet 112 or the like so that it can come in proximity to or away from the waterproof sheet 112 when the absorbent article 1 is fitted or removed.

The holding portion 114 has a substantially pocket-like space surrounded by the rear-side secured portion 113b of the top sheet 113 and the waterproof sheet 112, and receives and holds a rear-side portion 1a of the absorbent article 1.

The first and second securing portions 115 and 116 are provided to detachably secure a front-side portion of the top sheet 113 on the pants body 111 side (specifically, the waterproof sheet 112). The first securing portion 115 is secured by stitching, bonding, or the like to a front-side portion of the top sheet 113 on the outer side (on the side opposite from the skin-facing side). The second securing portion 116 is secured by stitching, bonding, or the like to a position that corresponds to the first securing portion 115 on the skin-facing side of the waterproof sheet 112 so that the first securing portion 115 is detachably secured. As for members used for the first securing portion 15 and the second securing portion 116, one may be made of a loop member provided with multiple loop structures and the other may be made of a hook member provided with multiple hook structures, for example.

Figure 8:
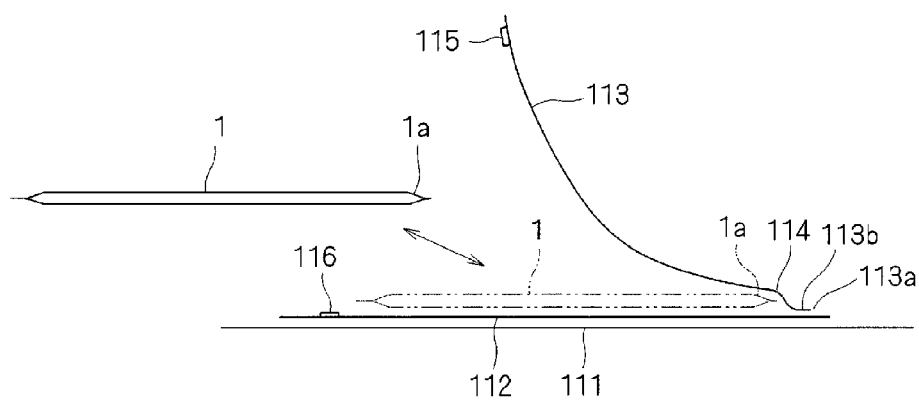
FIG. 8 is a view explaining operations at the time of fitting or removing an absorbent article in or from the incontinence pants in FIG. 5.

In the case where the absorbent article 1 is fitted in the incontinence pants 101, as illustrated in FIG. 8, the first and second securing portions 115 and 116 are released from their secured state, and the front-side portion of the top sheet 113 is lifted up so as to be separated from the waterproof sheet 112. Then, the absorbent article 1 is placed on the waterproof sheet 112 so the rear-side portion 1a of the absorbent article 1 is inserted into the holding portion 114, and the front-side portion of the top sheet 113 is closed so as to secure the first securing portion 115 to the second securing portion 116. Replacement or removal of the absorbent article 1 can be easily performed by releasing the first and second securing portions 115 and 116 from their secured state.

Figure 9:
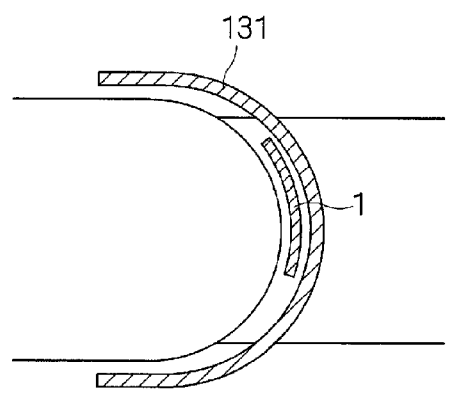
FIG. 9 illustrates an example of a use of the absorbent article in FIG. 1, showing how the absorbent article is arranged on the inside of a diaper.
Figure 10:
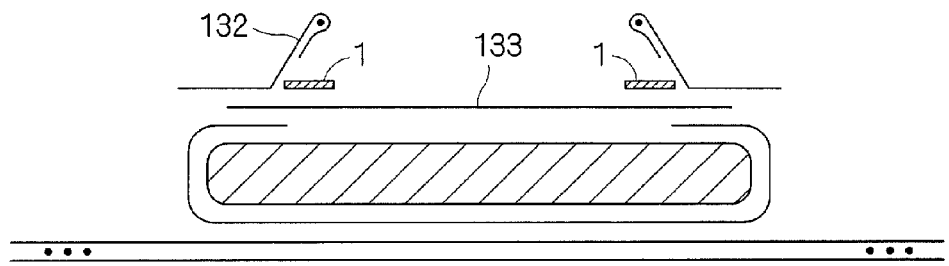
FIG. 10 is a cross-sectional view illustrating an example of arrangement in the case where the absorbent article in FIG. 1 is arranged on the inside of a diaper.

As another example of the use, as illustrated in FIG. 9, the absorbent article 1 according to the present embodiment may be arranged in any arbitrary number on the inner side of a diaper 131 in order to reinforce the absorbing capacity of the diaper 131, for example. Note that the diaper 131 may be of either a tape type or a pants type. Examples of positions where the absorbent article 1 is arranged include any part of a region that ranges from a discharging portion (e.g., private parts) over the crotch portion of a wearer in a space between the inner side of the diaper 131 and the skin side of the wearer. In this case, if leakguards 132 that stand up toward the skin side of a wearer are provided on the inner side of the diaper 131 as illustrated in FIG. 10, the absorbent article 1 may be arranged between the leakguards 132 and a top sheet 133 on the lateral inner sides of the leakguards 132 of the diaper 131. This prevents the absorbent article 1 from being displaced in position, dropping out through the leg holes, or the like. As another alternative, a holding structure for holding the absorbent article 1 may be provided on the skin-facing side of the diaper 131.

Moreover, for a wearer who has contracture of the body, a gap may be incurred between the diaper 131 and the body due to body atrophy or the like, and urine or the like may leak outside through the gap. In such a case, it is preferable that a urinary pad or the like be placed on the inside of the diaper 131 so as to prevent such incurrence of a gap, but in some cases, placing a urinary pad or the like may be difficult due to contracture of the body. Even in such a case where the placement of a urinary pad or the like is difficult due to contracture of the body, the absorbent article 1 can be inserted between the diaper 131 and the body, with a wearer wearing the diaper 131, so as to fill in the gap between the diaper 131 and the body.

Figure 11:
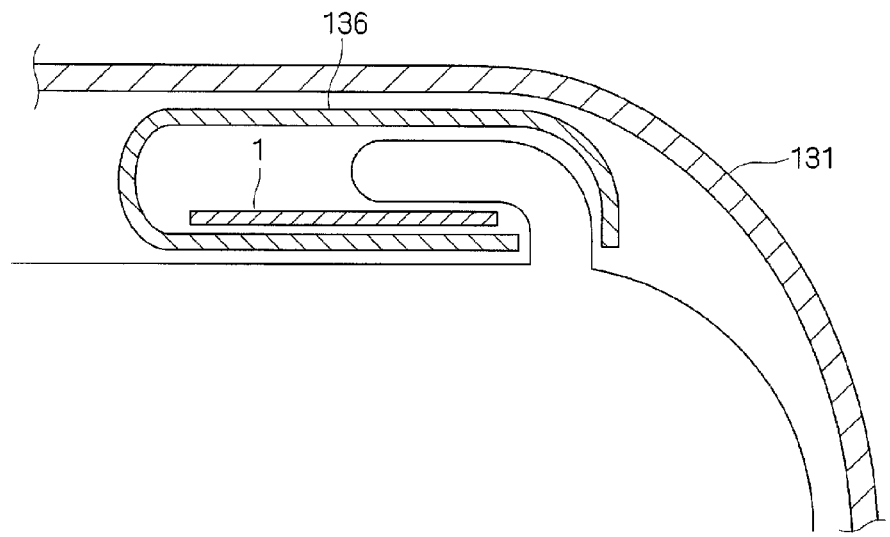
FIG. 11 illustrates another example of a use of the absorbent article in FIG. 1, showing how the absorbent article is inserted into a men's urine absorbent article of a substantially bag-like form.

Moreover, in another example of the use illustrated in FIG. 11, the absorbent article 1 according to the present embodiment is inserted into a men's urine absorbent article 136 of a substantially bag-like form in order to reinforce the urine-absorbing capacity of the urine absorbent article 136. The urine absorbent article 136 has a bag-like form and has an opening through which the penis of a wearer can be inserted. In many cases, such a urine absorbent article 136 is used in combination with the diaper 131.

As described above, in the absorbent article 1 according to the present embodiment, the multiple inner bag-like members 11 that contain the absorbent polymer 12 having a substantially granular or powder form in their inner accommodation spaces 17 are contained in a layered state in the outer bag-like member 13. This achieves the absorbent article 1 that provides sufficient absorbing capacity with a thin and compact structure and has good handleability when it is fitted in or removed from the above-mentioned incontinence pants 101, the abovementioned diaper 131, or the like.

In addition, the absorbent polymer 12 having a substantially granular or powder form is contained in each of the accommodation spaces 17 in the inner bag-like members 11 so as to be freely movable within the accommodation spaces 17. This ensures a sufficient space allowance for the swelling of the absorbent polymer 12 due to the absorption of excreted body fluids and consequently allows full use of the absorption performance of the absorbent polymer 12 without inhibiting the swelling of the absorbent polymer 12.

In addition, since the absorbent polymer 12 is freely movable in each of the accommodation spaces 17 in the inner bag-like members 11, the absorbent article 1 has a high degree of flexibility in its shape when it is fitted. As a result, the shape of the absorbent article 1 can be changed freely depending on where the absorbent article 1 is placed or the like, and accordingly the absorbent article 1 can be used for various purposes as described above. For example, as described above, the absorbent article 1 according to the present invention may be arranged in any arbitrary number on the inside of a diaper in order to reinforce the absorbing capacity of the diaper, for example.

In addition, the absorbent article 1 according to the present embodiment has a thin and compact structure as described above. This reduces unpleasantness, such as an oppressive sensation or a foreign body sensation, that a wearer may feel due to the arrangement of an absorbent article, for example in the case where the absorbent article 1 is arranged on the inside of a diaper, incontinence pants, or the like. For example, as described above, even in such a case where the placement of a urinary pad or the like is difficult for a wearer due to contracture of the body, the absorbent article 1 can be inserted into the space between the diaper and the body, while the wearer is wearing the diaper, so as to fill in the gap between the diaper and the body.

In addition, the multiple inner bag-like members 11 containing the absorbent polymer 12 are contained in the outer bag-like member 13. This eliminates the trouble of, for example, folding up the absorbent article 1 when the absorbent article 1 is fitted in incontinence pants, a diaper, or the like, and also eliminates the need to accommodate the absorbent article 1 in another bag-like body in order to keep the absorbent article 1 in a folded state, thus achieving good handleability at the time of fitting or removing the article.

In addition, since the absorbent article 1 has a substantially long-length shape extending in one direction, the absorbent article 1 can be arranged in a region along a crotch portion or the like of a wearer on the inside of incontinence pants, a diaper, or the like, without giving any unpleasantness to the wearer. In particular, as described above, for a wearer who has contracture of the body, the absorbent article 1 can be easily inserted into a crotch portion or the like of a wearer through a gap between the diaper and the skin side of the wearer, while the wearer is wearing the diaper.

In addition, since all materials for the inner bag-like members 11, the outer bag-like member 13, and the absorbent polymer 12 contained in the absorbent article 1 are biodegradable materials, the used absorbent article 1 can be disposed of by burial in the soil or the like. Moreover, since the absorbent polymer 12 is contained separately in the multiple inner bag-like members 11 and also contained separately in the multiple accommodation spaces 17 in each of the inner bag-like members 11, the absorbent polymer 12 can be distributed and biodegraded with efficiency without being grouped in clusters when the absorbent article 1 is disposed of by burial in the soil or the like. As a result, the whole absorbent article 1 can be biodegraded with efficiency.

In addition, according to the present embodiment, the first sheets 15 and 16 that form the inner bag-like member1 11 have a higher basis weight than the second sheets 18 and 19 that form the outer bag-like member 13. This allows a reduction in the basis weight of the second sheets 18 and 19 while preventing the absorbent polymer 12 from leaking outside through the first sheets 15 and 16 by narrowing gaps in the nonwoven fabric fiber of the first sheets 15 and 16. As a result, the material cost for the absorbent article 1 can be reduced.

In addition, since the basis weight of the first sheets 15 and 16 is made higher than the basis weight of the second sheets 18 and 19, the absorbent polymer 12 can be reliably sealed with the inner bag-like members 11 without using tissue paper having no degradability for the first sheets 15 and 16.

In addition, welding is used for every joint in the first sheets 15 and 16 for forming the inner bag-like members 11 and in the second sheets 18 and 19 for forming the outer bag-like member 13, and accordingly no adhesive is used. This avoids impairment of the biodegradability of the absorbent article 1 due to the use of an adhesive.

Note that, as a further variation of the absorbent article 1 according to the above-described embodiment, all materials for the inner bag-like members 11, the outer bag-like member 13, and the absorbent polymer 12 contained in the absorbent article 1 may be materials that have hydrolyzability in addition to biodegradability. This allows the hydrolytic degradation of the absorbent article 1 when the used absorbent article 1 is flushed down a toilet or the like, thus allowing the absorbent article 1 to be smoothly passed through a waste pipe or the like and thereby facilitating the progress of biodegradation.

Next, an absorbent article according to a second embodiment of the present invention will be described with reference to FIGS. 12 and 13. Note that in the description of the structure, effect, and any other feature of the absorbent article according to the present embodiment, the description of those parts that overlap with the contents of the absorbent article 1 according to the above-described first embodiment will be omitted where appropriate.

Figure 12:
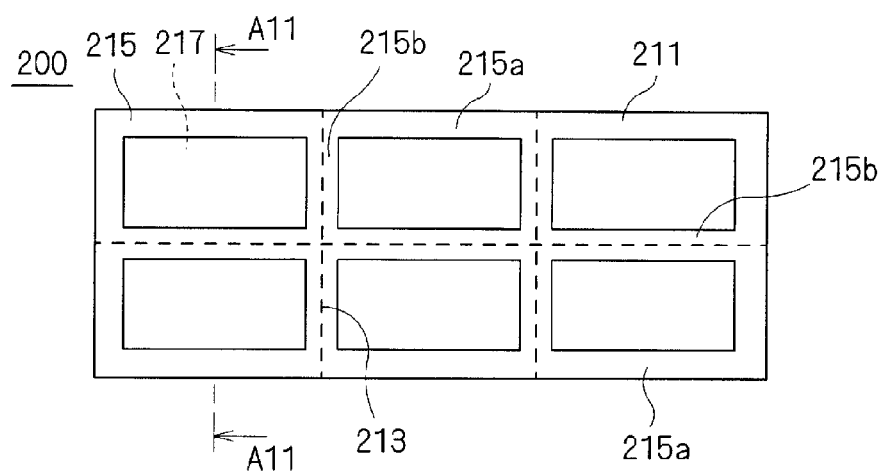
FIG. 12 is a plan view of an absorbent article according to a second embodiment of the present invention.
Figure 13:
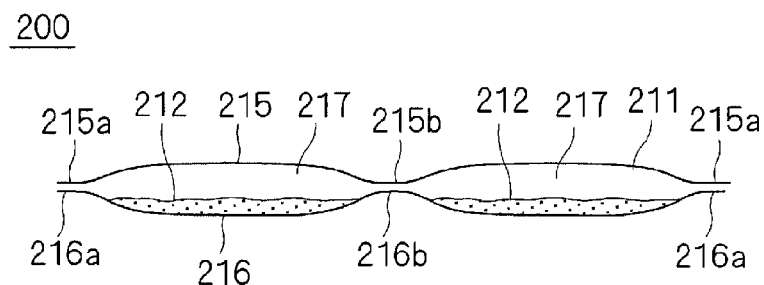
FIG. 13 is a view illustrating the structure in cross-section of the absorbent article taken along the line A11-A11 in FIG. 12.

An absorbent article 200 according to the present embodiment, as illustrated in FIG. 12 and FIG. 13, is configured to include a bag-like member 211, an absorbent polymer 212 contained in the bag-like member 211, a break portion 213 formed in the bag-like member 211. The absorbent article 200 is used to absorb excreted body fluids, such as moisture that is contained in urine or loose stools of a wearer, menstrual blood or the like. In the present embodiment, the absorbent article 200 is primarily used to absorb urine. All materials for the absorbent article 200 are biodegradable materials as will be described later, as in the case of the absorbent article 1 according to the above-described first embodiment.

The bag-like member 211 has a thin and substantially sheet-like form and is formed of two sheets 215 and 216 made of nonwoven fabric having biodegradability and fluid permeability. Inside the bag-like member 211, multiple accommodation spaces 217 are formed that are detached from the outside and separated from one another. The nonwoven fabric material for the sheets 215 and 216 may be polylactate, for example.

The sheets 215 and 216 have a substantially long-length rectangular plan shape extending in one direction. Outer edge portions 215a and 216a of the two sheets 215 and 216 are joined to each other by welding (heat welding or ultrasonic welding), and partition portions 215b and 216b that provide partitions between the adjacent multiple accommodation spaces 217 are joined to each other by welding (heat welding or ultrasonic welding). This produces the multiple accommodation spaces 217 that are detached from the outside and separated from one another, in the bag-like member 211. Note that, in the present embodiment, while the bag-like member 211 is formed of the two sheets 215 and 216, the bag-like member 211 may be formed by folding a single sheet 215 in two and joining the opposed outer edge portions 215a together.

The absorbent polymer 212 has biodegradability and a substantially granular or powder form and is contained in each of the accommodation spaces 217 in the bag-like member 211 so as to be freely movable within the accommodation spaces 217. The material for the absorbent polymer 212 may be polyaspartic acid, for example.

The break portion 213 is formed by weakening a part of the bag-like member 211 as compared to the other part so as to make it breakable, and is arranged so that the bag-like member 211 can be separated into multiple pieces. More specifically, the break portion 213 is provided along the partition portions 215b and 216b that provide partitions between the adjacent accommodation spaces 217 formed between the sheets 215 and 216 of the bag-like member 211. Moreover, the break portion 213 is, for example, a perforation in the sheets 215 and 216 or a thin portion of the sheets 215 and 216 that is thinner than the other portion. Examples of the method for forming the break portion 213 include a method using a mechanical machining means to perform partial cutting, punching, scoring, or the like on the sheets 215 and 216, and a method using a thermal heating means to mold a part of the sheets 215 and 216 by softening or melting through heating or the application of ultrasonic waves. Note that, in the case of using a thermal heating means, there is an advantage that the break portion 213 can be formed concurrently with the process of welding for forming the partition portions 215b and 216b in the sheets 215 and 216.

Such configured absorbent article 200 has a thin and substantially long-length shape extending in one direction as illustrated in FIG. 12. Quite similarly to the absorbent article 1 according to the above-described first embodiment, the absorbent article 200 according to the present embodiment can also be used in combination with the above-mentioned incontinence pants 101 illustrated in FIGS. 5 to 11.

As described above, in the absorbent article 200 according to the present embodiment, the break portion 213 is formed by weakening a part of the bag-like member 211 so as to make it breakable, and accordingly the bag-like member 211 can be separated into multiple pieces by breaking at the break portion 213. Hence, since the bag-like member 211 can be easily separated into small pieces by hand, the used absorbent article 200 can be easily disposed of by separating it into small pieces and flushing it down a toilet or the like. The absorbent article 200 that has been separated into small pieces and flushed down a toilet or the like can be biodegraded in a water-purifier tank or the like.

In addition, since the break portion 213 is provided along the partition portions 215*b* and 216*b* that provide partitions between the adjacent accommodation spaces 217 in the bag-like member 211, the break portion 213 can be formed in the bag-like member 211 without causing a decrease in strength or forming a hole or the like at a portion that forms the accommodation spaces 217 in the bag-like member 211.

In addition, since the break portion 213 is provided along the partition portions 215*b* and 216*b* of the bag-like member 211, when the used bag-like member 211 is separated at the break portion 213, the bag-like member 211 can be separated into small pieces without breaking a portion that forms the accommodation spaces 217 in the bag-like member 211. This avoids breakage of a portion that forms the accommodation spaces 27 in the bag-like member 211 at the time of separating the bag-like member 211, and thereby avoids inconvenience such as scattering of the absorbent polymer 212 contained in the accommodation spaces 217.

Also in the case of the absorbent article 200 according to the present embodiment, as in the case of the absorbent article 1 according to the above-described first embodiment, all materials for the bag-like member 211 and the absorbent polymer 212 contained in the absorbent article 200 may be materials that have hydrolyzability in addition to biodegradability.

REFERENCE SIGNS LIST

1 Absorbent article
11 Bag-like member
12 Absorbent polymer
13 Outer bag-like member
15, 16 First sheet
17 Accommodation space
18, 19 Second sheet
200 Absorbent article
211 Bag-like member
212 Absorbent polymer
213 Break portion
215, 216 Sheet
217 Accommodation space

The invention claimed is:

1. An absorbent article that absorbs excreted body fluids of a wearer, comprising:
    a bag-like member formed into a thin and substantially sheet-like form of a sheet being biodegradable and fluid permeable, and includes a plurality of accommodation spaces that is detached from the outside and separated from one another, wherein a partition portion is provided between the adjacent accommodation spaces;
    an absorbent polymer that is biodegradable, has a substantially granular or powder form, and is contained in each of the accommodation spaces in the bag-like member so as to be freely movable within the accommodation spaces; and
    a break portion that is formed at the partition portion by weakening a part of the bag-like member by a thermal heating means so as to make the part breakable, and is arranged so that the bag-like member is separated into a plurality of pieces, wherein the break portion is a thin portion of the sheets that is thinner than another portion of the partition portion.

2. The absorbent article according to claim 1, wherein the break portion is provided along a partition portion that provides a partition between each adjacent pair of the accommodation spaces in the bag-like member.

3. The absorbent article according to claim 1, wherein welding is used for every joint in the sheet for forming the bag-like member.

4. The absorbent article according to claim 1, wherein the absorbent article has a substantially long-length shape extending in one direction.

\* \* \* \* \*